US008604128B2

(12) United States Patent
Tang et al.

(10) Patent No.: US 8,604,128 B2
(45) Date of Patent: Dec. 10, 2013

(54) ROSIN-DERIVED CATIONIC COMPOUNDS AND POLYMERS ALONG WITH THEIR METHODS OF PREPARATION

(75) Inventors: Chuanbing Tang, Columbia, SC (US); Jifu Wang, Jiangsu Province (CN); Alan W. Decho, Columbia, SC (US); Yung Pin Chen, Columbia, SC (US)

(73) Assignee: University of South Carolina, Columbia, SC (US)

( * ) Notice: Subject to any disclaimer, the term of this patent is extended or adjusted under 35 U.S.C. 154(b) by 28 days.

(21) Appl. No.: 13/396,877

(22) Filed: Feb. 15, 2012

(65) Prior Publication Data
US 2012/0214950 A1   Aug. 23, 2012

Related U.S. Application Data
(60) Provisional application No. 61/463,304, filed on Feb. 15, 2011.

(51) Int. Cl.
*C08G 8/34* (2006.01)
(52) U.S. Cl.
USPC ............. 525/54.42; 162/164.6; 162/180; 525/54.4; 530/310; 530/212; 530/214; 530/221; 530/230; 530/231
(58) Field of Classification Search
USPC .............. 165/164.6, 180; 525/54.4, 54.42; 530/210, 212, 214, 221, 230, 231; 162/164.6, 180
See application file for complete search history.

(56) References Cited

U.S. PATENT DOCUMENTS
| | | | | |
|---|---|---|---|---|
| 4,219,382 | A | * | 8/1980 | Leffler ........................ 162/180 |
| 2011/0086979 | A1 | * | 4/2011 | Tang ......................... 525/54.45 |
| 2011/0303376 | A1 | * | 12/2011 | Nitzman et al. ............ 162/164.6 |

OTHER PUBLICATIONS
Schuller et al., Journal of Chemical and Engineering Data, 1967, p. 267-269.*
Gonis et al., Ind. Eng. Chem. Prod. Res. Develop., 1973, p. 326-327.*
Corma et al., "Chemical routes for the transformation of biomass into chemicals". Chemical Reviews 2007, 107, 2411-2502.
Dodds et al., "Chemicals from biomass". Science 2007, 318, 1250-1251.
Williams et al., "Polymers from renewable resources: a perspective for a special issue of polymer reviews". Polymer Reviews 2008, 48, 1-10.
Wool et al., "Affordable composites and plastics from renewable resources: part 1: synthesis of monomers and polymers". Advancing sustainability through green chemistry and engineering 2002, 177-204.
Zheng et al., "Controlled polymerization of rosin-derived monomers: a new class of renewable polymers", Polymer Preprints 2010, 51(2), 448-449.
Gabriel et al., "Infectious disease: connecting inate immunity to biocidal polymers". Materials Science and Engineering 2007, 57, 28-64.
Kenawy et al., "The Chemistry and Applications of Antimicrobial Polymers: A State-of-the-Art Review". Biomacromolecules 2007, 8, 5, 1359-1383.
Tashiro, T., "Antibacterial and Bacterium Adsorbing Macromolecules". Macromolecular Materials and Engineering 2001, 286, 63-87.
Yebra et al., "Antifouling technology-past, present and future steps towards efficient and environmentally friendly antifouling coatings". Progress in Organic Coatings 2004, 50, 75-104.
Zhang et al., "Polysulfobetaine-Grafted Surfaces as Environmentally Benign Ultralow Fouling Marine Coatings". Langmuir 2009, 25, 23, 13516-13521.
Maiti et al., "Renewable Resources From Forest Products For High Temperature Resistant Polymers". Polymer Application of Renewable-Resource Materials 1983, 129-147.
Maiti et al., "Rosin: a renewable resource for polymers and polymer chemicals", Progress in Polymer Science 1989, 14, 297-338.
Spessard et al., "Phytoalexin-line Activity of Abietic Acid and Its Derivatives". Journal of Agriculture and Food Chemistry 1995, 43, 1690-1694.
Jia et al., "Antimicrobial Activities of Rosin-based Gemini Cationic Surfactants". Chemistry and Industry of Forest Products 2010, 30, 1-4.
Do et al., "Synthesis and characteristics of photoactive-hydrogenated rosin epoxy methacrylate for pressure sensitive adhesives". Journal of Applied Polymer Science 2009, 111, 1172-1176.
Wang et al., "Study on the synthesis characterization and kinetic of bulk polymerization of disproportionated rosin (β-acryloxyl ethyl) ester". Journal of Applied Polymer Science 2009, 113, 3757-3765.
Zheng et al., "Well-defined renewable polymers derived from gum rosin", Macromolecules 2010, 43, 5922-5924.
Wilbon et al., "Renewable Rosin Acid-Degradable Capolactone Block Copolymers by Atom Transfer Radical Polymerization and Ring-Opeing Polymerization". Macromolecules 2010, 43, 8747-8754.
Bicu et al., "Diels-Alder polymerization of some derivatives of abietic acid". Die Angewandte Makromolekulare Chemie 1999, 264, 21-29.

(Continued)

*Primary Examiner* — Robert Jones, Jr.
(74) *Attorney, Agent, or Firm* — Dority & Manning, P.A.

(57) ABSTRACT

Methods for forming rosin-derived cationic compounds are provided. The method can include attaching a cationic group to a conjugated diene on a hydrophenathrene-based ring of a resin acid (e.g., levopimaric acid, abietic acid, dehydroabietic acid, or a mixture thereof) to form a rosin-derived cationic compound. Attaching the cationic group to the conjugated diene on the hydrophenathrene-based ring of the resin acid can be achieved via a Diels-Alder reaction of a dienophile with the hydrophenathrene-based ring of the resin acid. Rosin-derived cationic compounds are also provided. The rosin-derived cationic compound can include a cationic group attached to a conjugated diene on a hydrophenathrene-based ring of a resin acid, wherein the rosin-derived cationic compound further comprises a carboxylic acid group.

19 Claims, 8 Drawing Sheets

(56) References Cited

OTHER PUBLICATIONS

Bicu et al., "Water soluble polymers from Diels-Alder adducts of abietic acid as paper additives". Macromolecular Materials and Engineering 2000, 280/281, 47-53.

Bicu et al., "Polymers from a levopimaric acid-acrylonitrile Diels-Alder adduct: Synthesis and characterization". Journal of Polymer Science: Polymer Chemistry 2005, 43, 6308-6322.

* cited by examiner

ROSIN-DERIVED CATIONIC COMPOUNDS AND POLYMERS ALONG WITH THEIR METHODS OF PREPARATION

PRIORITY INFORMATION

The present application claims priority to U.S. Provisional Patent Application Ser. No. 61/463,304 titled "Rosin-Derived Cationic Compounds and Polymers and Their Methods of Preparation" filed on Feb. 15, 2011 by Tang, et al., which is incorporated by reference herein.

BACKGROUND

Synthetic plastics account for the use of 7% of fossil fuels in the world. The limited resources and rising price of fossil fuels present a challenge to seek developing renewable resources for manufacturing of "green" plastics. However, applications of renewable polymers lag significantly behind petrochemical-derived polymers, partially because of limitations in the monomer resources and the derived polymers with controlled properties.

As such, synthesis of renewable compounds and polymer-based materials from natural resources has attracted significant attentions, as these compounds and materials have the promise to replace compounds and plastics derived from petroleum chemicals. Cationic compounds have many applications such as antimicrobials, biocides, antibiotics, drug, surfactants, etc. Cationic polymers have many applications such as antimicrobial materials, antifouling coatings, packaging materials, surfactants, for use in water sanitation and purification, and in drug delivery, etc.

Produced in quantities of more than one million tons annually, rosin (including gum rosin, wood rosin and tall rosin), whose major components are resin acids (or rosin acids) including abietic acid, levopimaric acid, hydroabietic acid, dehydroabietic acid, pimaric acid, is generally used as ingredients for inks, vanishes, adhesives, cosmetics, medicines, chewing gums, etc. Rosin acids have three characteristic functionalities: hydrophenanthrene rings, carboxylic acid, and conjugated dienes.

Rosin has been used as raw materials to prepare cationic compounds. For example, rosin has been widely used as raw materials to prepare polymeric materials, in which rosin moieties are placed either at the backbone or at the side groups. Radical polymerization has been used to prepare vinyl polymers, while condensation polymerization has produced many polymers. (See e.g., U.S. Patent Publication No. 2011/0086979 of Chuanbing Tang titled "Polymers Derived from Rosin and Their Methods of Preparation").

However, the cationic group is, in these methods, attached to the rosin moiety through the carboxylic acid group. Thus, the most readily functionalizable group of the rosin moiety (i.e., the carboxylic acid group) is no longer available for further reaction according to these methods. Such limited functionality hinders the usefulness of the polymers formed according to these methods.

As such, a need exists for methods of preparing cationic compounds and cationic polymers from rosin (e.g., resin acids) without utilizing the carboxylic acid group of the rosin moiety.

SUMMARY

Objects and advantages of the invention will be set forth in part in the following description, or may be obvious from the description, or may be learned through practice of the invention.

Methods are generally provided for forming rosin-derived cationic compounds. In one embodiment, the method can include attaching a cationic group to a conjugated diene on a hydrophenathrene-based ring of a resin acid (e.g., levopimaric acid, abietic acid, dehydroabietic acid, or a mixture thereof) to form a rosin-derived cationic compound. For example, attaching the cationic group to the conjugated diene on the hydrophenathrene-based ring of the resin acid can comprise reacting a dienophile with the hydrophenathrene-based ring of the resin acid via a Diels-Alder reaction.

In one particular embodiment, the rosin-derived cationic compound can include a carboxylic acid group. As such, the method can further include reacting the carboxylic acid group on the rosin-derived cationic compound with a polymerizable group to form a functionalized rosin-derived cationic compound having a polymerizable functional group. The method can, in one embodiment, then further include polymerizing a plurality of the functionalized rosin-derived cationic compounds having a polymerizable functional group (e.g., a vinyl group) via controlled polymerization into a polymeric material, wherein each polymer defines a functional end group (e.g., a vinyl group), and wherein the polymeric material has a polydispersity index of about 1 to about 1.5 (e.g., about 1.05 to about 1.45).

For example, the method can further include reacting the carboxylic acid group on the rosin-derived cationic compound with an amine to form the functionalized rosin-derived cationic compound having the vinyl functional group. Alternatively, the method can further include reacting the carboxylic acid group on the rosin-derived cationic compound with an alcohol (e.g., hydroxyalkyl (meth)acrylate, such as hydroxyalkyl methacrylate) to form the functionalized resin acid having a vinyl functional group.

The plurality of rosin-derived cationic compounds can be, in particular embodiments, polymerized via controlled living polymerization. For example, controlled living polymerization can be atom transfer radical polymerization, wherein the rosin-derived cationic compounds are polymerized in a polymerization solution comprising the rosin-derived cationic compound, an initiator (e.g., an organic halide such as an alkyl halide), a ligand, and a catalyst (e.g., copper(I)). Alternatively, controlled living polymerization can be reversible addition-fragmentation chain transfer polymerization, wherein the rosin-derived cationic compounds are polymerized in a polymerization solution comprising the rosin-derived cationic compound, an initiator (e.g., azobisisobutyronitrile, 4,4'-azobis(4-cyanovaleric acid), or combinations thereof), and a chain transfer agent (e.g., a thiocarbonylthio compound).

Rosin-derived cationic compounds are also generally provided, such as those formed according to any of the presently disclosed methods. In one embodiment, the rosin-derived cationic compound can include a cationic group attached to a conjugated diene on a hydrophenathrene-based ring of a resin acid, wherein the rosin-derived cationic compound further comprises a carboxylic acid group.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which.

DEFINITIONS

Figure 1:
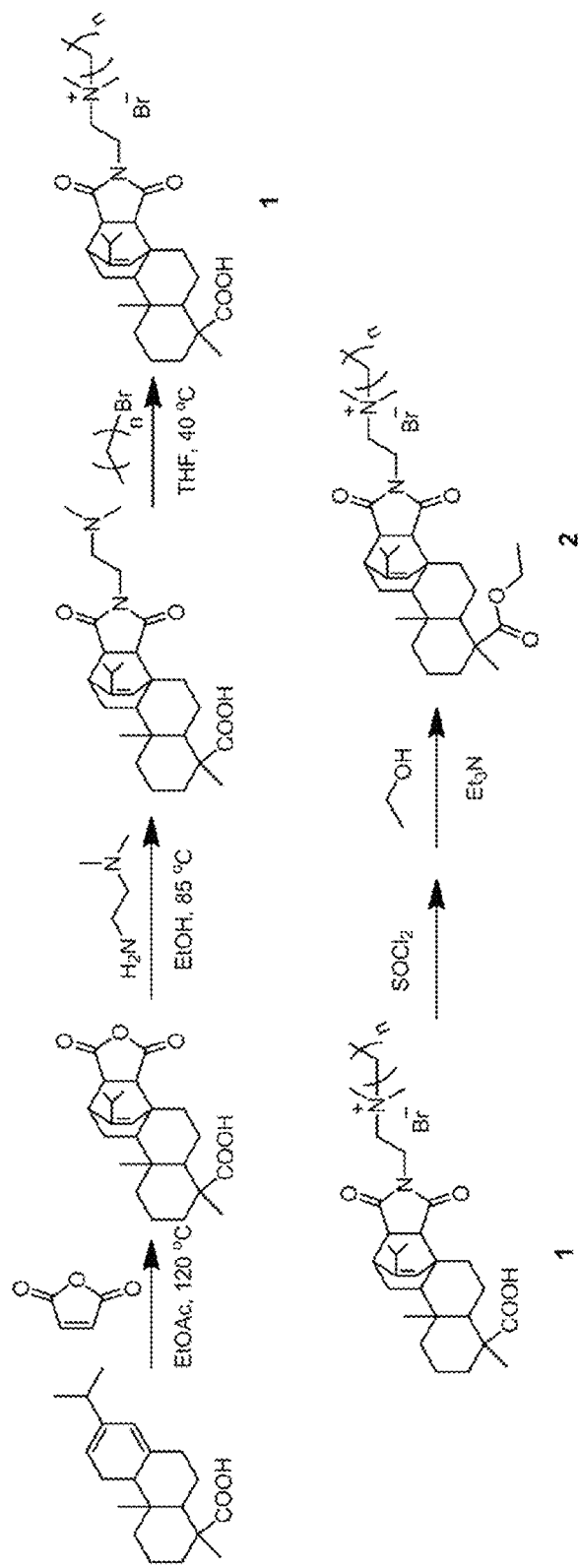
FIG. 1 shows an exemplary reaction method for synthesis of quaternary ammonium-containing rosin acid 1 and rosin ester 2.

As used herein, the term "polymer" generally includes, but is not limited to, homopolymers; copolymers, such as, for example, block, graft, random and alternating copolymers; and terpolymers; and blends and modifications thereof. Furthermore, unless otherwise specifically limited, the term "polymer" shall include all possible geometrical configurations of the material. These configurations include, but are not limited to isotactic, syndiotactic, and atatic symmetries.

The term "organic" is used herein to pertaining to a class of chemical compounds that are comprised of carbon atoms. For example, an "organic polymer" is a polymer that includes carbon atoms in the polymer backbone.

The "number average molecular weight" ($M_n$) is readily calculated by one of ordinary skill in the art, and generally refers to the ordinary arithmetic mean or average of the molecular weights of the individual macromolecules. It is determined by measuring the molecular weight of n polymer molecules, summing the weights, and dividing by n, such as represented in the formula:

$$\overline{M}_n = \frac{\sum_i N_i M_i}{\sum_i N_i}$$

where $N_i$ is the number of molecules of molecular weight $M_i$. The number average molecular weight of a polymer can be determined by gel permeation chromatography and all colligative methods, like vapor pressure osmometry or end-group determination.

The "weight average molecular weight" ($M_w$) is readily calculated by one of ordinary skill in the art, and generally refers to:

$$\overline{M}_w = \frac{\sum_i N_i M_i^2}{\sum_i N_i M_i}$$

where $N_i$ is the number of molecules of molecular weight $M_i$. The weight average molecular weight can be determined by gel permeation chromatography, light scattering, small angle neutron scattering (SANS) and X-ray scattering.

The polydispersity index (PDI) is a measure of the distribution of molecular mass in a given polymer sample. The PDI calculated is the weight average molecular weight divided by the number average molecular weight (i.e., PDI=$M_w/M_n$). It indicates the distribution of individual molecular masses in a batch of polymers. The PDI has a value equal to or greater than 1, but as the polymer chains approach uniform chain length, the PDI approaches unity (i.e., 1).

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention covers such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Generally speaking, the preparation of rosin-derived cationic compounds and cationic polymers is disclosed through functionalization of conjugated dienes of rosin moieties. Compositions are also generally disclosed of rosin-containing cationic compounds and polymers, along with methods of their formation and use.

Through these methods, rosin components (e.g., resin acids) can be integrated as part of renewable monomer units, and the cationic group can be part of rosin moiety. The cationic group can be quaternary ammonium, phosphonium, sulfonium, or a mixture thereof. The rosin-containing cationic compounds can have various applications such as antimicrobial reagents, biocides, antibiotics, drug, surfactants, etc.

Homopolymers can also be formed according to certain embodiments that can contain rosin-derived cationic units, where the units can be: (a) non-degradable monomers such as acrylates, methacrylates, acrylamides, styrenes; (b) degradable monomers such as caprolactone, lactide, glycolic acid, hydroxyalkanoic acids, hydroxybutyric acid, hydroxyvaleric acid, and trimethylene carbonate; or the like.

Rosin-containing cationic polymers for organic/inorganic nanocomposites can also be formed according to certain embodiments. Such rosin-containing cationic polymers can be star copolymers, grafted copolymers, etc. Rosin-containing cationic polymers can have various applications such as antimicrobial materials, antifouling coatings, packaging materials, surfactants, for use in water sanitation and purification, and in drug delivery, etc.

The properties of rosin-containing cationic polymers can be tuned by changing the molecular weight, compositions and chemical structures of each segment.

Rosin is a renewable biomass that includes resin acids (or rosin acids), such as levopimaric acid, abietic acid, hydroabietic acid, dehydroabietic acid, maleopimaric acid, etc. Such resin acids are used as substrates to prepare cationic compounds and/or cationic polymers. Thus, an entirely new approach is generally provided to develop rosin-containing cationic compounds and cationic polymers in applications such as drugs, antibiotics, antimicrobial materials, antifouling coatings, packaging materials, surfactants, for use in water sanitation and purification, and in drug delivery, etc. Successful implementation of these cationic compounds and cationic polymers can also provide a replacement of some of petrochemical-based chemicals and polymers, thus reducing consumption of major synthetic polymers derived from fossil fuels.

In particular embodiments, methods are provided for preparing rosin-containing cationic compounds and cationic polymers, where: the cationic compounds contain at least part of molecules derived from rosin; the cationic homopolymers contain rosin-derived side groups; the cationic block copolymers, graft copolymers, star copolymers and/or organic/inorganic hybrids contain at least one segment derived from rosin; the cationic block copolymers, graft copolymers, star copolymers and/or organic/inorganic hybrids contain at least one polymerized monomer derived from rosin and rosin-derived side groups; the cationic homopolymers, block copolymers, graft copolymers, star copolymers and/or organic/inorganic hybrids have controllable compositions, and molecular weight; and combinations thereof.

I. Rosin-Derived Resin Acids

Rosin's major components include resin acids, which can be obtained from pine trees and other plants, in a number of isomeric forms. Generally, the resin acids have a three ring structure (e.g., a hydrophenanthrene-based three ring structure) with a carboxylic acid functional group (i.e., —COOH). Prevalent resin acids include, but are not limited to, abietic acid, neoabietic acid, dehydroabietic acid, palustric acid, levopimaric acid, pimaric acid, isopimaric acids, etc. Nearly all resin acids have the same basic skeleton of a 3-ring fused system with the empirical formula $C_{19}H_{29}COOH$.

Six particularly suitable resin acids for use as monomers in the presently disclosed methods and polymers include levopimaric acid, abietic acid, dehydroabietic acid, hydroabietic acid, pimaric acid, isopimaric acid, and mixtures thereof due to their availability commercially at various purities. Each of these resin acids have a carboxylic acid group (i.e., R—COOH) attached to the hydrophenanthrene-based rings.

However, resin acids having conjugated dienes on its hydrophenanthrene-based ring are particularly suitable for reaction with a cationic group while leaving the carboxylic acid group unchanged in the resulting rosin-derived cationic compound. The chemical structures of particularly suitable resin acids, which have conjugated dienes on its hydrophenanthrene-based ring, are provided below and are generally known in the art:

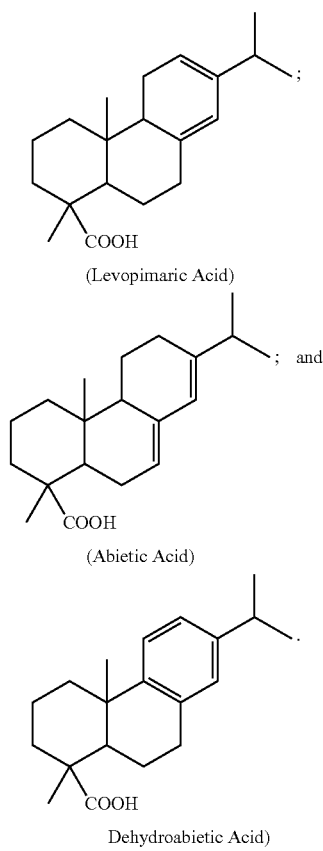

As shown, each of these resin acids has conjugated dienes on its hydrophenathrene-based ring.

The resin acid or mixture of resin acids (collectively referred to as "resin acid(s)") can be purified through standard techniques to provide a substantially pure resin acid(s) starting material for the polymers. For example, the resin acid or mixture of resin acids can be purified to at least about 95% by weight, such as at least about 98% by weight.

In particular embodiments, the resin acid or mixture of resin acids can be purified to be about 99% by weight to substantially free from other materials. As used herein, the term "substantially free" means no more than an insignificant trace amount present and encompasses completely free (e.g., 0% by weight up to about 0.0001% by weight). Thus, most or substantially all of the other organic material in the rosin can be separated from the resin acid(s) prior to functionalization.

In alternative embodiments, the resin acid(s) can be utilized collectively in their natural rosin form.

II. Functionalized Resin Acids

In one particular embodiment, a functionalized resin acid is provided that still includes its carboxylic acid group. For example, a resin acid that has at least two conjugated dienes on its hydrophenathrene-based ring can be reacted with a dienophile via a Diels-Alder reaction. In a typical Diels-Alder reaction, the dienophile has an electron-withdrawing group conjugated to an alkene, though this feature is not exclusive of Diels-Alder dienophiles. In certain embodiments, the dienophile can be activated by a Lewis acid such as niobium pentachloride. Additionally, the Diels-Alder reaction can be carried out in the presence of ethyl acetate.

Suitable dienophiles for reaction with the conjugated dienes of the resin acid include, but are not limited to, maleic anhydride, cyclohexenone, styrene, acrylic acid, methacrylic acid, acrylamide, methacrylamide, or mixtures and/or derivatives thereof.

Figure 3:
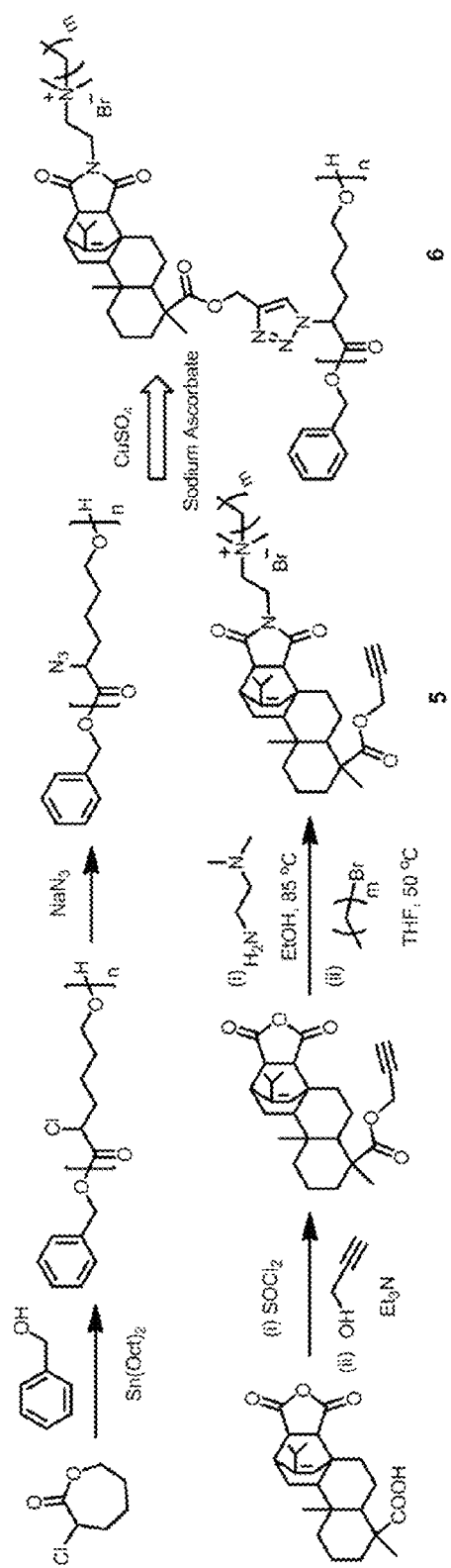
FIG. 3 shows an exemplary reaction method synthesis of degradable quaternary ammonium-containing rosin-derived polycaprolactone 6.
Figure 4:
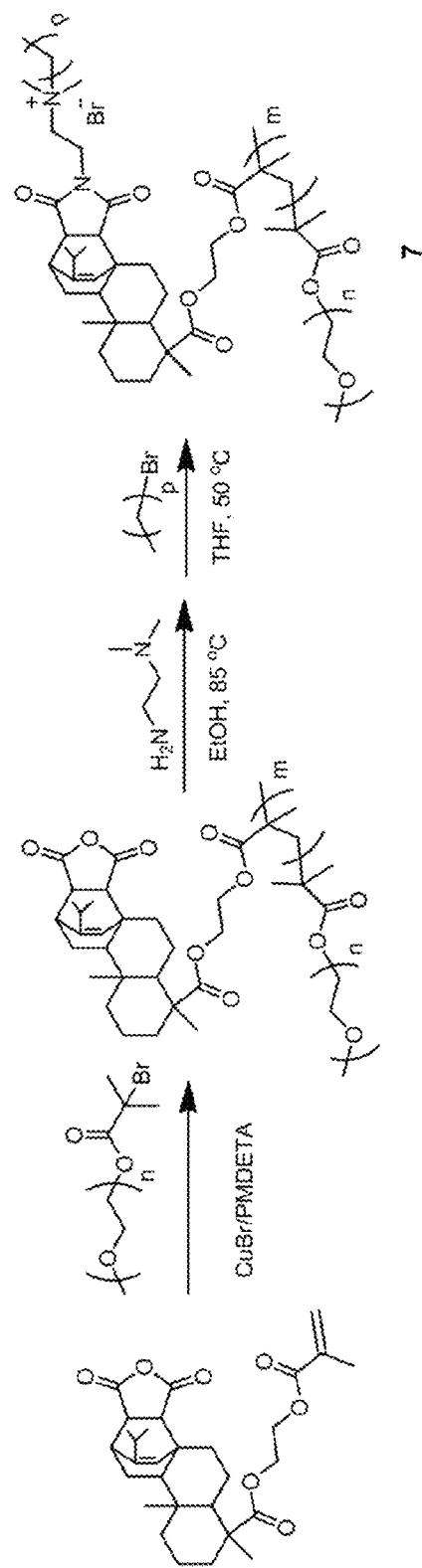
FIG. 4 shows an exemplary reaction method synthesis of quaternary ammonium-containing rosin-derived block copolymer 7.
Figure 5:
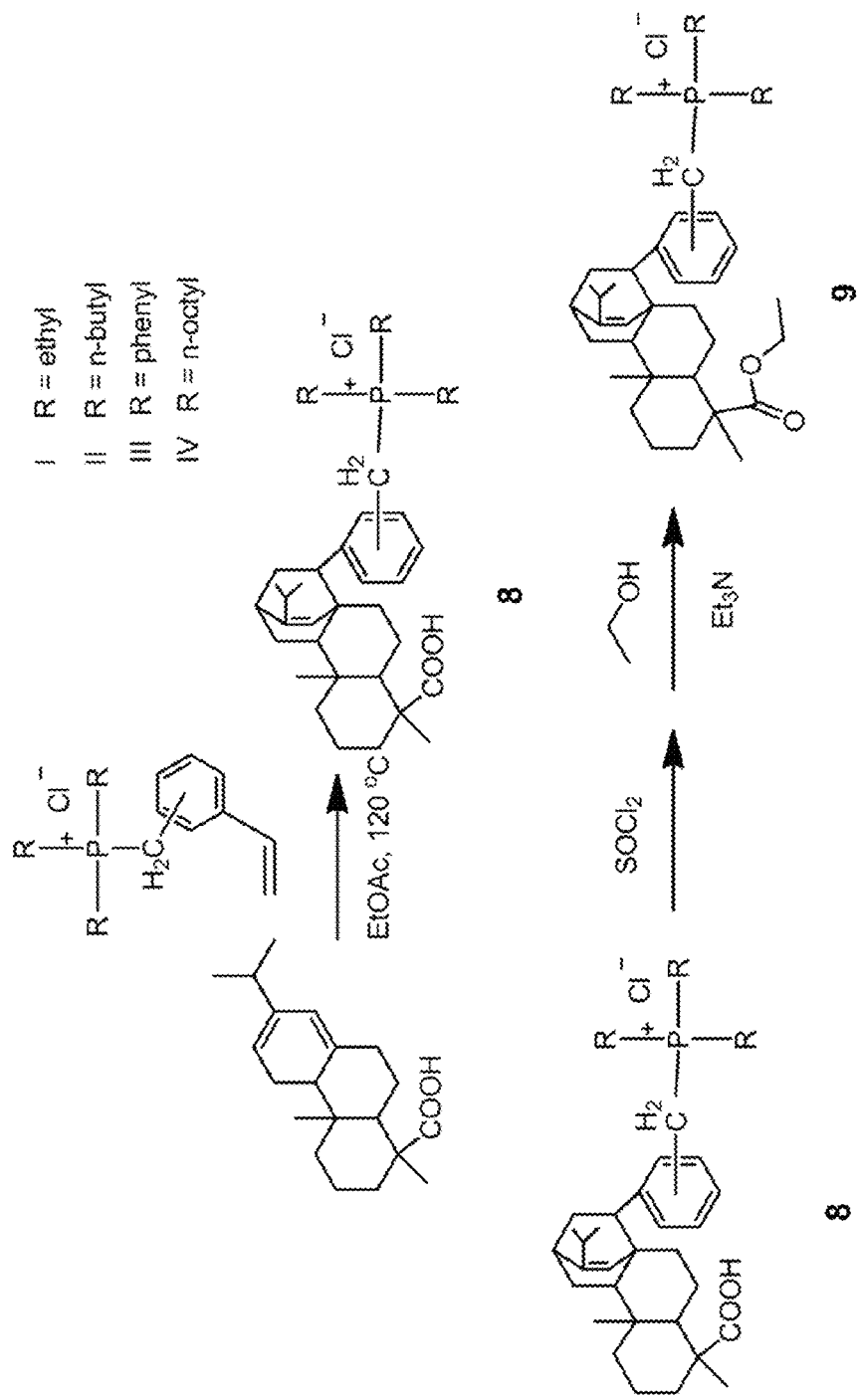
FIG. 5 shows an exemplary reaction method synthesis of phosphonium salts-containing rosin acid 8 and rosin ester 9.
Figure 6:
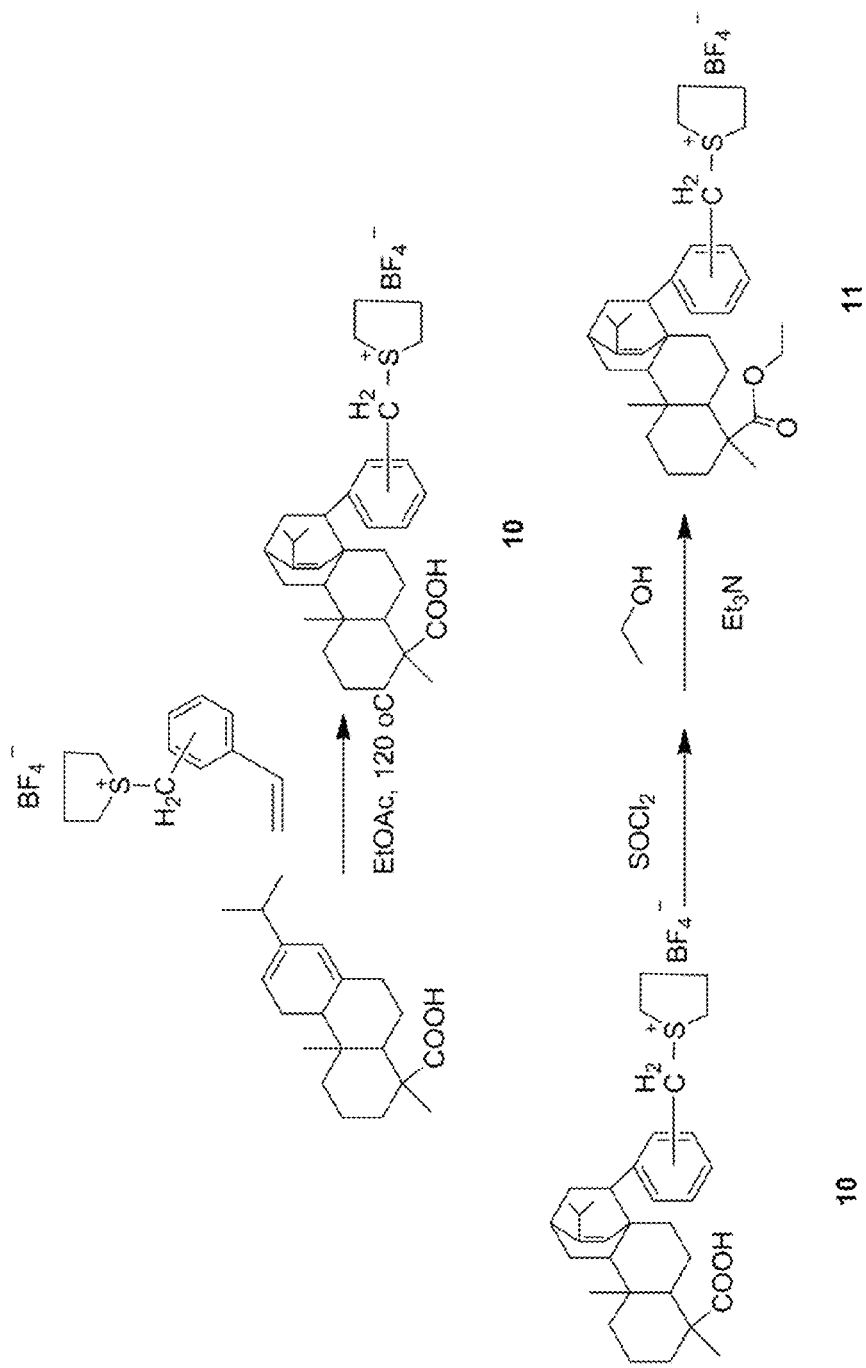
FIG. 6 shows an exemplary reaction method synthesis of sulfonium salts-containing rosin acid 10 and rosin ester 11.

For example, FIGS. 1-4 show exemplary reactions involving maleic anhydride with the conjugated dienes of the resin acid. Alternatively, FIGS. 5 and 6 show exemplary reactions involving a styrene derivative with the conjugated dienes of the resin acid.

III. Rosin-Derived Cationic Compounds

Rosin-derived cationic compounds and their synthesis are generally described in one particular embodiment. Specifically, methods are disclosed of preparing cationic compounds and cationic polymers from rosin (e.g., resin acids) without utilizing the carboxylic acid group of the rosin moiety, along with the resulting compounds. For instance, the cationic group (e.g., a quaternary ammonium group) can be attached through functionalization of conjugated dienes of rosin moieties.

In particular, the resin acid(s) can be functionalized with polymerizable groups, such as vinyl groups (e.g., an acrylate group, a methacrylate group, etc.) or strained ring functional groups (e.g., cyclic ester groups like caprolactone or lactide, a norbornene group, a cyclopentene group, etc.). Specifically, the conjugated dienes on its hydrophenathrene-based ring can be functionalized into the polymerizable groups.

For example, FIG. 1 shows a quaternary ammonium-containing rosin acid 1 prepared through a Diels-Alder reaction between levopimaric acid and maleic anhydride followed by an amidation and a quaternization reaction. The quaternary ammonium-containing rosin acid 1 can be further converted to the quaternary ammonium-containing rosin ester 2 through an esterification reaction. Although shown as a cationic quaternary ammonium unit in the reaction of FIG. 1, this unit can be substituted or replaced with other cationic units, e.g. phosphonium, sulfonium.

In one embodiment, the rosin unit can be derived through thermal isomerization of other acid forms, e.g. abietic acid. Likewise, the ester group can be replaced by other groups such as alcohols, amides, ethers, alkyl halides, epoxides, aldehydes, alkenes, alkynes, etc.

Thus, FIG. 1 illustrates a scheme for one particular embodiment—the case of quaternary ammonium-containing rosin acid (1) and rosin ester (2), as described further in the Examples.

IV. Rosin-Derived Monomers

Rosin-derived monomers can also be formed utilizing the rosin-derived cationic compounds. For example, the carboxylic acid group on the rosin-derived cationic compound can be functionalized into monomers containing the Diels-Alder adduct (e.g., an anhydride adduct) and a polymerizable functional group. For instance, the polymerizable functional group can be attached to the rosin-derived cationic compound via its carboxylic acid group. Particularly suitable methods for attaching a polymerizable functional group to the carboxylic acid group of a resin acid are described in U.S. Patent Publication No. 2011/0086979 of Chuanbing Tang titled "Polymers Derived from Rosin and Their Methods of Preparation," which is incorporated by reference herein.

V. Polymerization of Rosin-Derived Monomers

Polymers that can be formed according to the presently disclosed methods, include, but are not limited to, homopolymers, block copolymers, graft polymers, star polymers, organic polymers/inorganic hybrids, etc. In one particular embodiment, these polymer compositions can also have controlled molecular weight and/or can be formed from rosin derivatives and degradable polymers. Degradable polymers comprise at least one of repeating units: caprolactone, lactide, lactic acid, glycolic acid, hydroxyalkanoic acids, hydroxybutyric acid, hydroxyvaleric acid, trimethylene carbonate, dicarboxylic acid anhydrides, butylene succinate, and butylene adipate.

Additionally, in certain embodiments, well-defined rosin-derived polymers and their methods of production are provided. Thus, a synergistic strategy has been developed to form well-defined polymers from a renewable resource—rosin, which is an exudate from pine trees and other plants. Accordingly, well-defined rosin-derived polymers with controlled molecular weight, low polydispersity, chemical topologies and end group functionality can be developed to provide tailored properties for applications in the areas of thermoplastic resins, thermoplastic elastomers, adhesives, printing inks, paper-sizing, varnishes, coatings, nanocomposites, shape memory materials, anti-fouling materials, nanoporous membranes, etc.

The presently disclosed methods can allow for controllable molecular weight, low polydispersity and varied chemical topologies and chain functionality of the polymers. Thus, a broad strategy is generally disclosed allowing for the development of well-defined polymers derived from renewable resources, which can provide access to diverse polymers that rosin offers, but with controlled structures and molecular weight. Successful implementation of these rosin-based polymers can lead to replacement of petrochemical-based polymers, thus reducing consumption of major synthetic polymers from fossil fuels.

More particularly, methods are provided for preparing well-defined polymers from rosin based materials (e.g., rosin based monomers, such as modified resin acids). The well-defined polymers can include block copolymers, random copolymers, graft copolymers, star copolymer, or organic/inorganic hybrids that contain at least one polymerized monomer derived from rosin. Such well-defined polymers have controllable compositions, controllable molecular weight, a narrow molecular weight distribution, and end group functionality.

Rosin-derived polymers developed according to the present disclosure can have applications ranging from thermoplastic resins, thermoplastic elastomers, varnishes, wax, paper sizing, adhesives, coatings, printing inks to shape memory polymers, nanocomposites, pharmaceutics, anti-fouling, nanoporous membrane, etc.

In certain embodiments, the functionalized resin acid(s) can be subjected to controlled polymerizations, such as controlled living polymerizations (CLPs) or controlled ring-opening polymerizations. Through the use of these controlled polymerizations, polymers can be produced with low polydispersity, high functionality (e.g., a terminal functional group), and diverse architectures. Thus, these methods are ideal for block polymer and/or graft polymer synthesis.

Controlled living polymerization generally refers to chain growth polymerization which proceeds with significantly suppressed termination or chain transfer steps. Thus, polymerization in CLP proceeds until all monomer units have been consumed, and the addition of monomer results in continued polymerization, making CLP ideal for block polymer and graft polymer synthesis. The molecular weight of the resulting polymer is generally a linear function of conversion so that the polymeric chains are initiated and grow substantially uniformly. Thus, CLPs provide precise control on molecular structures, functionality and compositions. Thus, these polymers can be tuned with desirable compositions and architectures.

Controlled living polymerizations can be used to produce block copolymers because CLP can leave a functional terminal group on the polymer formed (e.g., a halogen functional group). For example, in the copolymerize of two monomers (A and B) allowing A to polymerize via CLP will exhaust the monomer in solution with minimal termination. After monomer A is fully reacted, the addition of monomer B will result in a block copolymer.

Controlled ring-opening polymerizations can utilize suitable catalysts such as tin(II) to open the rings of monomers to form a polymer.

The functionalized resin acid(s) can be polymerized alone (e.g., as a single resin acid or a combination of multiple resin acids) or with other monomers (e.g., styrene, methacrylate, acrylate, lactide, caprolactone, etc., or combinations thereof). As such, in specific embodiments, block copolymers, random copolymers, graft copolymers, star copolymer or organic/inorganic hybrids can each bear other monomer units selected from olefins, conjugated dienes, methacrylates, styrenes, acrylates, acrylamides, and acrylonitriles, esters, ethers, urethanes, ureas, amides and other functional monomer units thereof.

Specific polymerization techniques can be utilized to form the well-defined polymers, as discussed in greater detail below.

A. Atom Transfer Radical Polymerization

Atom transfer radical polymerization (ATRP) is an example of a living radical polymerization. The control is achieved through an activation-deactivation process, in which most of the reaction species are in dormant format, thus significantly reducing chain termination reaction. The four major components of ATRP include the monomer, initiator, ligand, and catalyst, ATRP is particularly useful where the functionalized resin acid(s) have a vinyl functional group (e.g., a (meth)acrylate group).

Organic halides are particularly suitable initiators, such as alkyl halides (e.g., alkyl bromides, alkyl chlorides, etc.). For instance, in one particular embodiment, the alkyl halide can be ethyl 2-bromoisobutyrate. The shape or structure of the initiator can also determine the architecture of the resulting polymer. For example, initiators with multiple alkyl halide groups on a single core can lead to a star-like polymer shape.

The catalyst can determine the equilibrium constant between the active and dormant species during polymerization, leading to control of the polymerization rate and the equilibrium constant. In one particular embodiment, the catalyst is a metal having two accessible oxidation states that are separated by one electron, and a reasonable affinity for halogens. One particularly suitable metal catalyst for ATRP is copper (I).

The ligands can be linear amines or pyridine-based amines.

Depending on the target molecular weight of final polymers, the monomer to initiator ratios can range from less than about 10 to more than about 1,000 (e.g., about 10 to about 1,000). Other reaction parameters can be varied to control the molecular weight of the final polymers, such as solvent selection, reaction temperature, and reaction time. For instance, solvents can include conventional organic solvents such as tetrahydrofuran, toluene, dimethylformamide, anisole, acetonitrile, dichloromethane, etc. The reaction temperature can range from room temperature (e.g., about 20° C.) to about 120° C. The reaction time can be from less than about 1 h to about 48 h.

B. Reversible Addition-Fragmentation Chain Transfer Polymerization

Reversible Addition-Fragmentation chain Transfer polymerization (RAFT) is another type of controlled radical polymerization. RAFT polymerization uses thiocarbonylthio compounds, such as dithioesters, dithiocarbamates, trithiocarbonates, and xanthates, in order to mediate the polymerization via a reversible chain-transfer process. RAFT polymerization can be performed by simply adding a chosen quantity of appropriate RAFT agents (thiocarbonylthio compounds) to a conventional free radical polymerization. RAFT polymerization is particularly useful where the functionalized resin acid(s) have a vinyl functional group (e.g., a (meth) acrylate group).

Typically, a RAFT polymerization system includes the monomer, an initiator, and a RAFT agent (also referred to as a chain transfer agent). Because of the low concentration of the RAFT agent in the system, the concentration of the initiator is usually lower than in conventional radical polymerization. Suitable radical initiators can be azobisisobutyronitrile (AIBN), 4,4'-azobis(4-cyanovaleric acid) (ACVA), etc.

RAFT agents are generally thiocarbonylthio compounds, such as generally shown below:

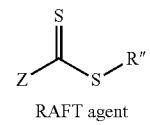

RAFT agent where the z group primarily stabilizes radical species added to the C=S bond and the R group is a good hemolytic leaving group which is able to initiate monomers. For example, the z group can be an aryl group (e.g., phenyl group, benzyl group, etc.), an alkyl group, etc. The R" group can be an organic chain terminating with a carboxylic acid group.

As stated, RAFT is a type of living polymerization involving a conventional radical polymerization in the presence of a reversible chain transfer reagent. Like other living radical polymerizations, there is minimized termination step in the RAFT process. The reaction is started by radical initators (e.g., AIBN). In this initiation step, the initiator reacts with a monomer unit to create a radical species which starts an active polymerizing chain. Then, the active chain reacts with the thiocarbonylthio compound, which kicks out the homolytic leaving group (R"). This is a reversible step, with an intermediate species capable of losing either the leaving group (R") or the active species. The leaving group radical then reacts with another monomer species, starting another active polymer chain. This active chain is then able to go through the addition-fragmentation or equilibration steps. The equilibration keeps the majority of the active propagating species into the dormant thiocarbonyl compound, limiting the possibility of chain termination. Thus, active polymer chains are in an equilibrium between the active and dormant species. While one polymer chain is in the dormant stage (bound to the thiocarbonyl compound), the other is active in polymerization.

By controlling the concentration of initiator and thiocarbonylthio compound, the molecular weight of the polymers can be controlled with low polydispersities.

Depending on the target molecular weight of final polymers, the monomer to RAFT agent ratios can range from about less than about 10 to more than about 1000 (e.g., about 10 to about 1,000). Other reaction parameters can be varied to control the molecular weight of the final polymers, such as solvent selection, reaction temperature, and reaction time. For instance, solvents can include conventional organic solvents such as tetrahydrofuran, toluene, dimethylformamide, anisole, acetonitrile, dichloromethane, etc. The reaction temperature can range from room temperature (e.g., about 20° C.) to about 120° C. The reaction time can be from less than about 1 h to about 48 h.

The RAFT process allows the synthesis of polymers with specific macromolecular architectures such as block, gradient, statistical, comb/brush, star, hyperbranched, and network copolymers.

Because RAFT polymerization is a form of living radical polymerization, it is ideal for synthesis of block copolymers. For example, in the copolymerization of two monomers (A and B) allowing A to polymerize via RAFT will exhaust the monomer in solution with significantly suppressed termination. After monomer A is fully reacted, the addition of monomer B will result in a block copolymer. One requirement for maintaining a narrow polydispersity in this type of copolymer is to have a chain transfer agent with a high transfer constant to the subsequent monomer (monomer B in the example).

Using a multifunctional RAFT agent can result in the formation of a star copolymer. RAFT differs from other forms of CLPs because the core of the copolymer can be introduced by functionalization of either the R group or the Z group. While utilizing the R group results in similar structures found using ATRP or NMP, the use of the Z group makes RAFT unique. When the Z group is used, the reactive polymeric arms are detached from the core while they grow and react back into the core for the chain-transfer reaction.

C. Nitroxide-Mediated Polymerization

Nitroxide-mediated polymerization (NMP) is another form of controlled living polymerization utilizing a nitroxide radical, such as shown below:

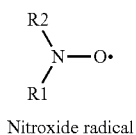

Nitroxide radical where R1 and R2 are, independently, organic groups (e.g., aryl groups such as phenyl groups, benzyl groups, etc.; alkyl groups, etc.). NMP is particularly useful where the functionalized resin acid(s) have a vinyl functional group (e.g., a (meth)acrylate group).

D. Ring-Opening Metathesis Polymerization

Ring-opening metathesis polymerization (ROMP) is a type of olefin metathesis polymerization. The driving force of the reaction is relief of ring strain in cyclic olefins (e.g. norbornene or cyclopentene) in the presence of a catalyst. The catalysts used in a ROMP reaction can include a wide variety of metals and range from a simple $RuCl_3$/alcohol mixture to Grubbs' catalyst.

In this embodiment, the functionalized resin acid can include a strained ring functional group, such as a norbornene functional group, a cyclopentene functional group, etc. to form the rosin derived polymers. For example, norbornene is a bridged cyclic hydrocarbon that has a cyclohexene ring bridged with a methylene group in the para position.

The ROMP catalytic cycle generally requires a strained cyclic structure because the driving force of the reaction is relief of ring strain. After formation of the metal-carbene species, the carbene attacks the double bond in the ring structure forming a highly strained metallacyclobutane intermediate. The ring then opens giving the beginning of the polymer: a linear chain double bonded to the metal with a terminal double bond as well. The new carbene reacts with the double bond on the next monomer, thus propagating the reaction.

E. Ring-Opening Polymerization

In one particular embodiment, where the functionalized resin acid includes a strained ring function group (e.g., a caprolactone or lactide), ring-opening polymerization (ROP) may be used to form the rosin derived polymers. For example, a rosin-substituted caprolcatone is a polymerizable ester, which can undergo polymerization with the aid of an alcohol as an initiator and a tin-based reagent as a catalyst.

VI. Rosin-Derived Polymers and Block Co-Polymers

Through CLP, the resulting polymeric material can include well-defined polymers, referencing the substantially low polydispersity index. For example, the resulting polymers can have a PDI of less than 1.5, such as about 1.05 to about 1.45.

The molecular weight of these resulting polymers can be controlled as desired. In most embodiments, the molecular weight of the resulting polymers can be about 2,000 g/mol to about 1,000,000 g/mole, such as about 10,000 g/mol to about 750,000 g/mole. However, in other embodiments, the molecular weight can be larger or smaller.

Generally, the composition of rosin-derived units (i.e., the functionalized resin acid(s) monomers) is primarily in the range of about 10% by weight to about 95% by weight (e.g., about 50% by weight to about 80% by weight). In one particular embodiment, the resulting polymer includes only functionalized resin acid(s) monomers (i.e., about 100% functionalized resin acid(s) monomers).

However, in alternative embodiments, these resulting polymers can bear other comonomers. Particularly suitable comonomers can include those with polymerizable functional groups (e.g., vinyl functionality), such as styrene, methacrylate, acrylate, lactide, caprolactone, etc, and combinations thereof.

In one particular embodiment, the functionalized resin acid(s) monomers can be used for preparation of block copolymers with two monomers (AB diblock copolymer or ABA triblock copolymers) or three monomers (ABC triblock copolymers).

In an alternative embodiment, the functionalized resin acid(s) monomers can be used for preparation of graft copolymers, such as (i) from a polymer backbone; (ii) from a curve surface such as silica nanoparticles; (iii) from a flat surface such as silicon wafer substrates, or the like.

Additionally, the functionalized resin acid(s) monomers can be used for preparation of star copolymers, for organic and/or inorganic nanocomposites, etc.

Rosin-derived block copolymers exhibit microphase separation, which can combine multifunctional properties from the constituent components. The properties can be tuned by changing the molecular weight, compositions and chemical structures of each segment.

In one particular embodiment, degradable polymers can be synthesized from rosin based materials. Such degradable polymers can have many applications including packaging materials, auto parts, drug delivery, tissue engineering, membrane, gas storage, etc. Additionally, the integration of rosin with degradable polymers can have several benefits: 1) more environmentally friendly, through the template of degradable polymers, degradation would produce residual rosin or rosin polymers, which have much lower molecular weight (therefore more compatible with environments) than those rosin polymers without degradation templates; 2) increased renewable capacity for non-renewable degradable polymers by increasing the volume of rosin in the degradable polymers; and 3) new thermal, mechanical and degradability properties originating from rosin moiety.

In particular, the functionalized resin acid(s) can be co-polymerized with degradable comonomers. As such, the resulting copolymers can include the rosin-derived units in about 10% by weight to about 90% by weight, while the degradable comonomers are present in about 10% by weight to about 90% by weight. Suitable degradable comonomers can include caprolactone, lactide, glycolic acid, hydroxyalkanoic acids, hydroxybutyric acid, hydroxyvaleric acid, trimethylene carbonate, etc., or combinations thereof. The comonomer can be used to form random copolymers, block copolymers, graft copolymers, etc.

For example, poly(2-chloro-ε-caprolactone) homopolymers can be prepared through ring-opening polymerization, and then converted into poly(2-azide-ε-caprolactone) homopolymers, which click with alkyne containing dehydroabietic moiety. Polycaprolactone is degraded under acidic conditions or bio conditions. The caprolactone unit can be replaced by other degradable units, e.g. lactide, glycolic acid, hydroxyalkanoic acids, hydroxybutyric acid, hydroxyvaleric acid, and trimethylene carbonate. The molecular weight of these polymers can be in the range of about 2,000 g/mol to about 1,000,000 g/mole.

VII. Exemplary Polymerizations

Figure 2:
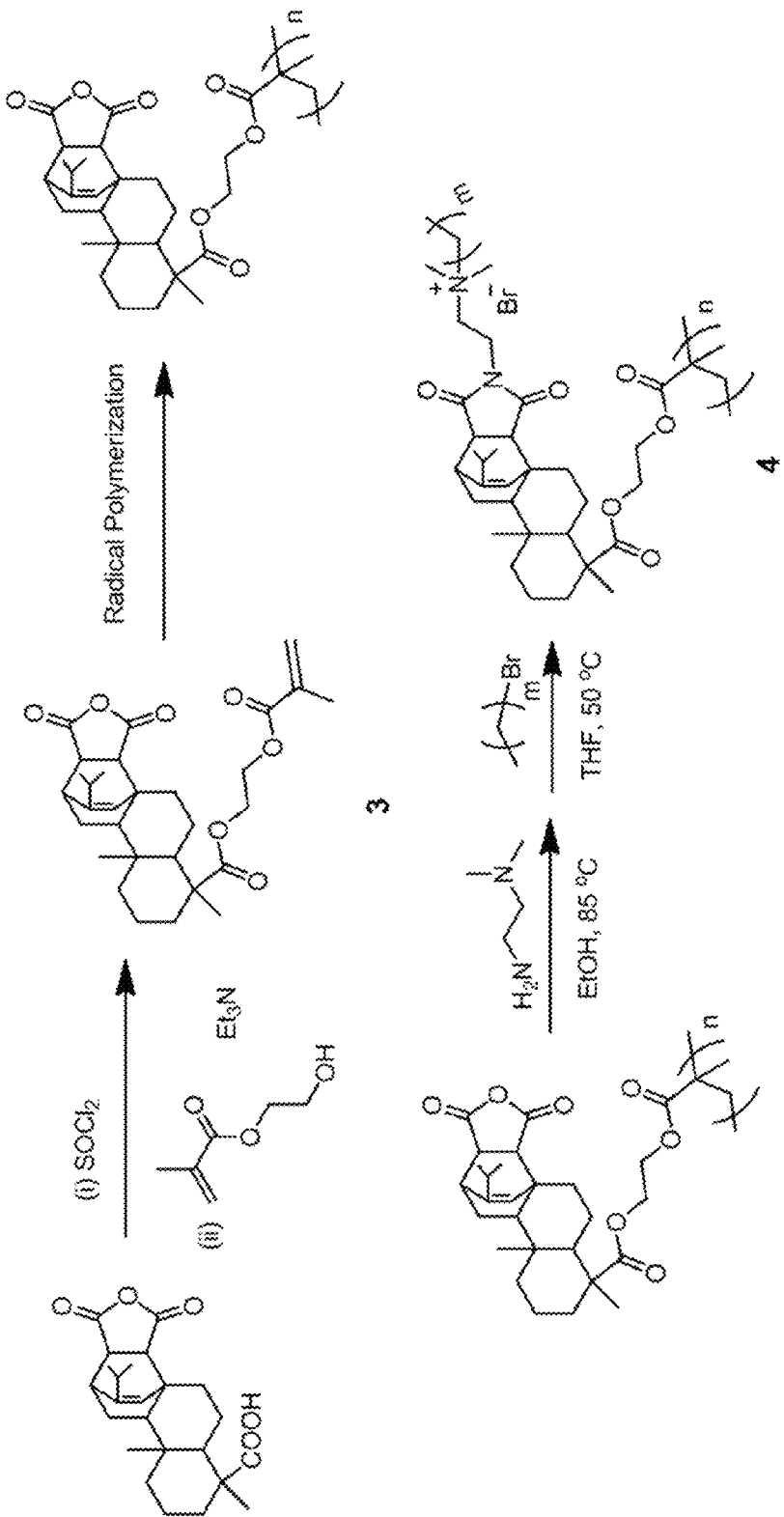
FIG. 2 shows an exemplary reaction method for synthesis of quaternary ammonium-containing rosin-derived methacrylate polymer 4.

In one embodiment, the synthesis of rosin-derived cationic acrylic homopolymers with controlled molecular weight is generally provided. For example as shown in FIG. 2, methacrylate homopolymers are prepared from methacrylate monomers containing Diels-Alder adduct (anhydride) 3 through the radical polymerization. The polymer can then be converted into quaternary ammonium-containing rosin-derived methacrylate polymer 4 by an amidation and a quaternization reaction. The methacrylate unit can be replaced by other monomer units, e.g. acrylates, acrylamides, styrenes. Additionally, the cationic quaternary ammonium unit can be replaced by other cationic units (e.g. phosphonium, sulfonium, etc.). The rosin unit can be derived from other acid forms, e.g. abietic acid, through thermal isomerization.

The polymer 4 can be also prepared by post-polymerization modification, e.g. esterification reaction between poly(2-hydroxyethyl methacrylate) and compound 2. The molecular weight of these polymers is primarily in the range of 1,000-500,000 g/mole. FIG. 2 illustrates a scheme for one particular embodiment—the case of quaternary ammonium-containing rosin-derived methacrylate polymer 4.

Additionally, the synthesis of rosin-derived cationic degradable homopolymers with controlled molecular weight is generally provided. For example, FIG. 3 shows poly(2-chloro-ε-caprolactone) homopolymers can be prepared through ring opening polymerization. Poly(2-chloro-ε-caprolactone) homopolymers are then converted into poly(2-azide-ε-caprolactone) homopolymers, which then click with alkyne-containing rosin-derived quaternary ammonium 5, yielding degradable quaternary ammonium-containing rosin-derived polycaprolactone 6. Polycaprolactone is degraded under acidic conditions or composting conditions. The caprolactone unit can be replaced by other degradable units, e.g. lactide, glycolic acid, hydroxyalkanoic acids, hydroxybutyric acid, hydroxyvaleric acid, and trimethylene carbonate. Rosin unit can be derived from other acid forms, e.g. abietic acid, levopimaric acid, hydroabietic acid, pimaric acid. The molecular weight of these polymers is primarily in the range of 1,000-500,000 g/mole. FIG. 3 illustrates a scheme for one particular embodiment—the case of quaternary ammonium-containing rosin-derived polycaprolactone 6.

The synthesis of rosin-containing cationic block copolymers with controlled molecular weight and compositions is also generally provided. For example, FIG. 4 shows a block copolymer 7 comprising of quaternary ammonium-containing rosin-derived methacrylate segment and ethylene oxide segment that can be prepared through sequential atom transfer radical polymerization. These polymers can be tuned with desirable compositions. The molecular weight of these polymers is primarily in the range of 1,000-500,000 g/mole. The composition of rosin-derived units is primarily in the range of 10-90 wt %. The novel method involves a polymeric composition comprising tunable rosin compositions and chemical structures, FIG. 4 illustrates a scheme for one particular embodiment—the case of diblock copolymers of rosin-derived methacrylate and ethylene oxide.

VIII. Resin Acid-Derived Antimicrobial Agents

Robust resin acid-derived antimicrobial agents are also generally provided that exhibit excellent antimicrobial activities against a broad spectrum of bacteria (6 Gram-positive and 7 Gram-negative) with selective lysis of microbial membranes over mammalian membranes. The hydrophobicity and unique structures of resin acids can be determining factors in dictating the antimicrobial activity.

Bacterial contamination of food, drinking water and medical implants and devices has posed serious threats to human health and, in some cases, has caused widespread outbreaks of infectious diseases. Development of effective antibacterial agents has attracted much attention as they are capable of killing pathogenic microorganisms or preventing biofouling of surfaces (e.g. coating to ship hulls). Currently the majority of synthetic antimicrobial materials are compounds or polymers having cationic functional groups, which promote rapid sorption onto the negatively-charged cell surfaces of microorganisms. Many synthetic and non-degradable polymers such as polynorbornene, polyacrylates, polyarylamides, polyesters, poly(β-lactam) and pyridinium polymers have exhibited efficient antimicrobial activities.

In one particular embodiment, natural resin acid-derived cationic compounds and polymers are disclosed that exhibit high antimicrobial activities against a broad spectrum of bacteria while maintaining selective lysis on bacterial cell membranes without inducing significant haemolysis of red blood cells over a wide range of concentrations. It is believed that the excellent antimicrobial activities of resin acid-derived antimicrobial compounds and polymers are a combination of resin acids and their cationic charge.

Figure 8:
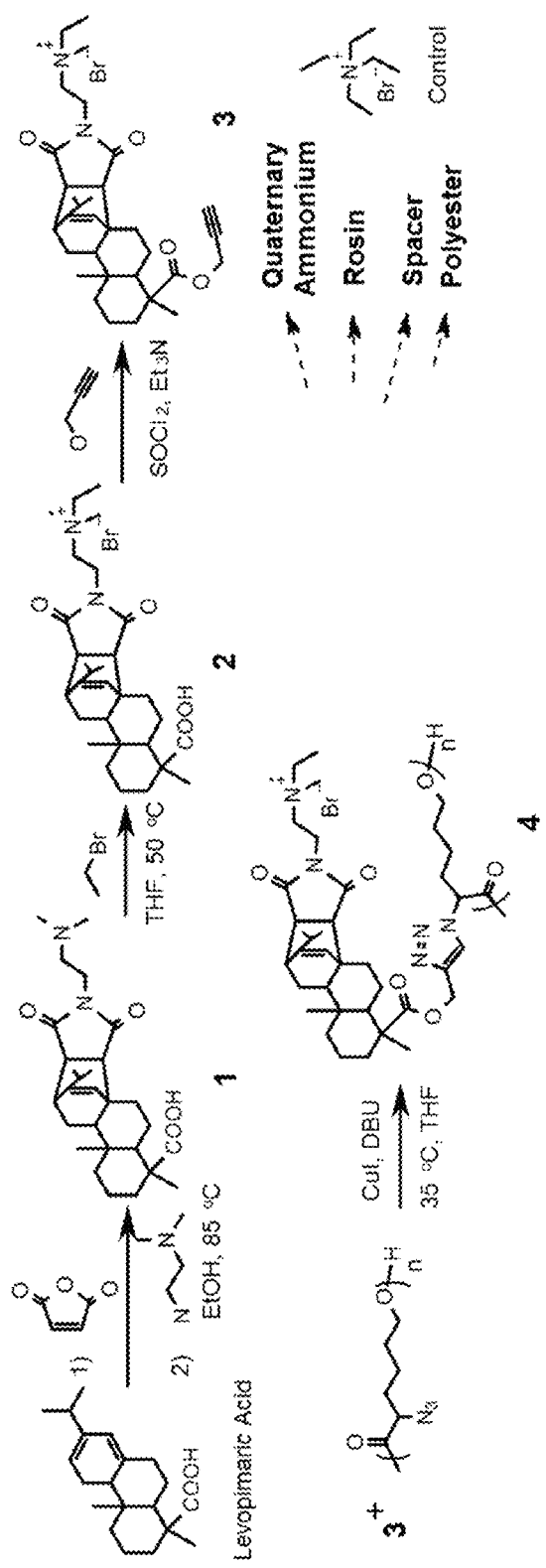
FIG. 8 shows an exemplary scheme for the synthesis of quaternary ammonium-containing resin acid-derived antimicrobial compounds and polymers.

For example, resin acids can be used as a hydrophobic component in antimicrobial agents, and be used to influence the relationship between antimicrobial activity and hydrophilic-hydrophobic balance. As shown in the scheme of FIG. 8, the synthesis can be started with a highly efficient Diels-Alder reaction between a resin acid (shown as levopimaric acid) and maleic anhydride to produce maleopimaric add, followed by an amidation reaction with N,N-dimethylaminoethylamine to yield compound 1. Quaternary ammonium-containing resin acid 2 can then be prepared by a quaternization reaction between 1 and ethyl bromide. An esterification between compound 2 and propargyl alcohol can lead to the formation of quaternary ammonium-containing resin propargyl ester 3.

In parallel, azide-substituted poly(ε-caprolactone) (PCL) can be prepared in a multi-step route by first preparing a quaternary ammonium-containing resin acid-substituted PCL 4 via a click reaction between compound 3 and azide-substituted PCL in dimethylformamide with the use of CuI/DBU (1,8-diazabicyclo[5.4.0]undec-7-ene) as catalysts.

EXAMPLES

Examples of such rosin-containing cationic compounds and cationic polymers are described below.

Example 1

Example 1 describes the preparation of quaternary ammonium-containing rosin acids and rosin esters, according to the exemplary method shown in FIG. 1. The synthesis for the integration of quaternary ammonium group into the moiety of rosin is described as follows: The abietic acid, maleic anhydride and acetic acid were mixed in a round bottom flask under a nitrogen atmosphere and heated at 120° C. for 12 h to yield levopimaric acid. The levopimaric acid is stirred with dimethylethylenediamine at 85° C. for 8 h, yielding a rosin-derived tertiary ammonium derivative, which is then stirred with an alkyl halide (e.g. bromoethane, bromohexane, bromooctane and bromododecane) at 40° C. in tetrahydrofuran for 48 h to yield quaternary ammonium-containing rosin acid 1. The quaternary ammonium-containing rosin acid is dissolved in thionyl chloride and refluxed for 12 h. Then, thionyl chloride is removed by reduced pressure distillation. Ethanol, triethylamine and tetrahydrofuran are added and stirred at room temperature for 24 h to yield the ethyl ester of quaternary ammonium-containing rosin acid 2.

Example 2

This example is to prepare quaternary ammonium-containing rosin-derived methacrylate polymers, according to the exemplary method shown in FIG. 2. The method involves the synthesis of methacrylate monomers containing Diels-Alder adduct (anhydride) by esterification, and homopolymer by free radical polymerization. Following the amidation and quaternization reactions, the quaternary ammonium group is introduced. A typical procedure for the synthesis is described as follows: levopimaric acid is dissolved in thionyl chloride and refluxed for 12 h. Thionyl chloride is removed by reduced pressure distillation. The methacrylate monomer containing Diels-Alder adduct (anhydride) 3 is obtained by the addition of excess 2-hydroxyethyl methacrylate (2-HEMA) and using triethylamine as catalyst. The homopolymer is prepared by the radical polymerization of monomer 3 in the presence of the toluene and azoisobutyronitrile (AIBN). The homopolymer is dissolved in ethanol and then added with the dimethylethylenediamine. The mixture is stirred at 85° C. for 5 h and precipitated in diethyl ether to obtain the rosin-derived tertiary ammonium homopolymer. The quaternary ammonium unit 4 is then introduced by the reaction between the rosin-derived tertiary ammonium homopolymer and alkyl halide (e.g. bromoethane, bromohexane, bromooctane and bromododecane) in tetrahydrofuran at 40° C. for 48 h.

Example 3

This example is to prepare degradable quaternary ammonium-containing rosin-derived polycaprolactone, according to the exemplary method shown in FIG. 3. The synthesis comprises of two parallel routes. First, 2-chloro-ε-caprolactone and benzyl alcohol, and toluene are placed in a Schlenk flask, a solution of tin(II) 2-ethylhexanoate is added and the flask is purged with nitrogen. The mixture is stirred at 120° C. for 12 h to yield poly(2-chloro-ε-caprolactone) homopolymers. The poly(2-chloro-ε-caprolactone) is stirred with sodium azide in dimethylformamide for 24 h, yielding poly(2-azide-ε-caprolactone). Secondly, levopimaric acid is dissolved in thionyl chloride and refluxed for 12 h and the thionyl chloride was removed by reduced pressure distillation. Propargyl alcohol, triethylamine and tetrahydrofuran are added and stirred at room temperature for 24 h to yield the propargyl ester of maleopimaric acid. Amidation reactions between propargyl ester of maleopimaric acid and dimethylethylenediamine at 85° C. for 5 h, and followed by a reaction with alkyl halide (e.g. bromoethane, bromohexane, bromooctane and bromododecane) at 40° C. in tetrahydrofuran for 48 h yield an alkyne-containing rosin-derived quaternary ammonium 5. At last, click reaction between poly(2-azide-ε-caprolactone) and compound 5 in tetrahydrofuran at 35° C. by using CuI as the catalyst results in polycaprolactone with a quaternary ammonium-containing rosin-derivative 6.

Example 4

This example is to prepare quaternary ammonium-containing rosin-derived block copolymers, according to the exemplary method shown in FIG. 4. Methacrylate monomers containing Diels-Alder adduct (anhydride) 3 (see Example 2), PEG macroinitiator, and N,N,N',N'',N''-pentamethyldiethylenetriamine (PMDETA) are mixed in a Schlenk flask and purged with nitrogen. After three cycles of freeze-pump-thaw, CuBr is added into flask and stirred at 80° C. for 24 h to yield block copolymer 7. The introduction of quaternary ammonium group to the block copolymer is similar to the quaternization in Example 2. The block copolymer and dimethylethylenediamine are dissolved in ethanol and refluxed at 85° C. for 5 h, and precipitated in diethyl ether to obtain the rosin-derived tertiary ammonium block copolymer. The quaternary ammonium unit is introduced by the reaction between the rosin-derived tertiary ammonium block copolymer and alkyl halide (e.g. bromoethane, bromohexane, bromooctane and bromododecane) at 40° C. in tetrahydrofuran for 48 h.

Example 5

This example is to prepare phosphonium salts-containing rosin acid and its ester, according to the exemplary method shown in FIG. 5). The synthesis is described as: The levopimaric acid, triethyl-3-[(and 4-)vinylbenzyl]phosphonium chloride (I) (or II, III, IV) and acetic acid are mixed and heated (120° C.) for 12 h in a round bottom flask under a nitrogen atmosphere to yield phosphonium salts-containing rosin acid 8. Synthesis of the ester of phosphonium salts-containing rosin acid 9 is similar to the esterification reaction in Example 1.

Example 6

This example is to prepare sulfonium salts-containing rosin acid and its ester, according to the exemplary method shown in FIG. 6). The procedure of synthesis is similar to Example 5 and described as follows: A mixture of levopimaric acid, vinyl benzyl sulfonium salt and acetic acid is stirred at 120° C. for 12 h in round bottom flask under the protection of nitrogen to yield the sulfonium salts-containing rosin acid 10. According the method similar to Example 1, sulfonium salts-containing rosin acid is then converted into an ester 11.

Application Example

Antimicrobials 1

Tests for antimicrobial activities were carried out using rosin-derived quaternary ammonium 1 and their polymer 4 with a number-average molecular weight of $7.5 \times 10^5$ g/mol. The antimicrobial susceptibilities of several Gram-negative bacteria (e.g. *Pseudomonas aeruginosa*, *Escherichia coli*, *Enterobacter aerogenes*, and *Klebsiella pneumonia*) and Gram-positive bacteria (*Staphylococcus aureus* and *Bacillus*

Figure 7:
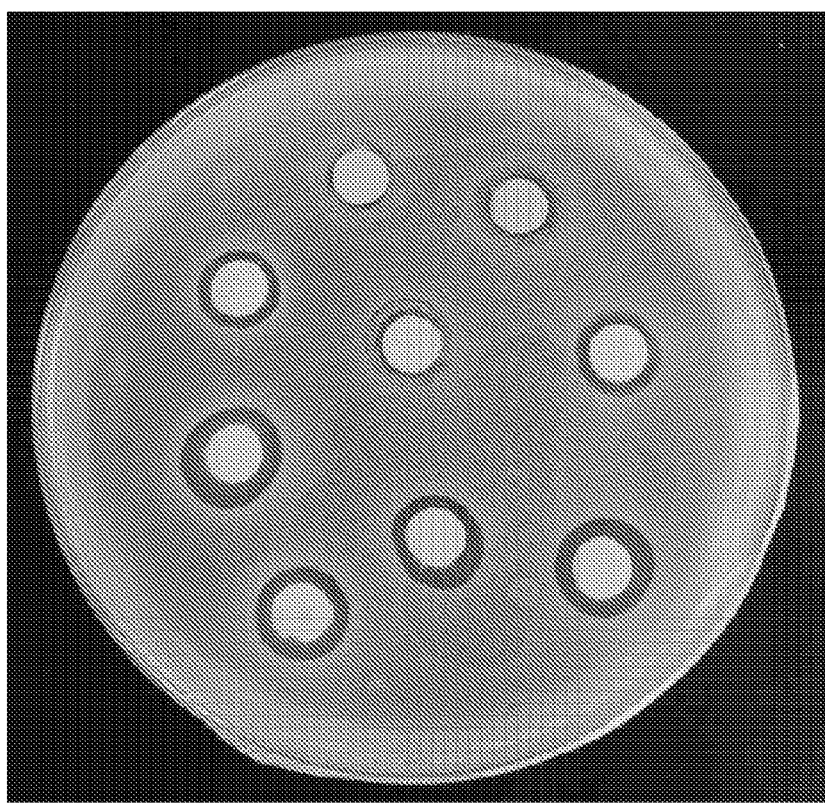
FIG. 7 shows an Agar diffusion method to test antibacterial activity of rosin-derived quaternary ammonium and its polymer (at different concentrations) against *Staphylococcus aureus*.

*cereus*) were determined. These strains were purified at laboratory and maintained at −70° C. in a 1:1 mixture of glycerol and dimethylsulfoxide (DMSO). To conduct the assays, a small volume of actively-growing cultures of each bacterial strain is spread on agar plates, and incubated at 28° C. for 24 h to form a 'bacterial lawn' covering the plate surface. Then 6 mm (dia) filter discs are added to the surface, and 30 ul samples (containing each compound at several concentrations dissolved in DMSO) are applied to the disc surfaces, and the plates are incubated. The development of a clear inhibition zone around a disk is indicative of the compounds ability to kill bacteria (FIG. 7).

Application Example

Antimicrobials 2

Referring to FIG. 8, the antimicrobial activities of the resin acid-derived compounds (2 and 3) and polymer (4) were prepared and tested against a range of pathogenic and non-pathogenic microorganisms, including Gram-negative bacteria (*Pseudomonas aeruginosa, Escherichia coli, Klebsiella pneumoniae, Proteus vulgaris, Enterobacter agglomerans, Salmonella typhimurium, Alcaligenes faecalis*) and Gram-positive bacteria (*Staphylococcus aureus, Bacillus cereus, Streptococcus pyogenes, Micrococcus luteus, Mycobacterium smegmatis*). Initially, broth dilution and disk-diffusion methods were compared in determining the minimal inhibitory concentrations (MICs) of 2, 3 and 4 against *S. aureus, E. coli, K. pneumoniae*, and *P. aeruginosa* as proxies for evaluating their antimicrobial activities. The results showed that most MIC values for a given bacterium obtained by compounds 2 and 3 and polymer 4 showed significantly lower MIC obtained by disk-diffusion method than the one by broth Considering the potential applications of antimicrobial compounds and polymers as coatings for food packaging, medical implants and devices, and antifouling surfaces, all subsequent MIC determinations were carried out using the disk-diffusion method. Results of the assays indicated that both resin acid-derived quaternary ammonium compounds (including acid-based 2 and ester-based 3) and their polymers 4, as shown in FIG. 8, exhibited strong antimicrobial activities against both Gram-positive bacteria with MICs ranging between 0.7-10.1 µM, and Gram-negative bacteria with MICs between 3-40 µM. These MIC values are comparable or better than many new systems developed recently. Thus, these results illustrated a highly efficient antimicrobial activity of these materials against a broad spectrum of bacteria.

The time-dependent efficiency of antimicrobial activities of compound 3 and polymer 4, of FIG. 8, against *S. aureus* were then investigated. It was observed that antimicrobial effects of the compound 3 were very rapid, with approximately 90% of *S. aureus* cells being killed within 1 h, while >75% strains were killed by polymer 4 in 6 h. It is believed, without wishing to be bound by theory, that the excellent antimicrobial activities are derived from hydrophobicity of the hydrophenanthrene moiety, which likely enhanced the penetration of the compounds/polymers into cell membranes and subsequent killing of the bacteria. This was further confirmed with control experiments, in which a quaternary ammonium compound without the resin acid moiety, tetraethylammonium bromide (TEAB), showed no activities against both Gram-positive and Gram-negative bacteria. In addition, controls consisting resin acid-derived compound 1 without quaternary ammonium also exhibited negligible activities against all bacterial strains, and highlighted the importance of the quaternary ammonium moiety in the observed antimicrobial activities. Results clearly showed the visual effect of different materials against *S. aureus* using the Agar diffusion method.

To further confirm that the antimicrobial activities were not caused by residual copper catalysts and solvents (i.e. methanol), control experiments were carried out using these reagents against different bacterial strains. However, both copper catalysts and methanol did not exhibit significant toxicity, again indicating that the antimicrobial activities originated from resin acid-derived compounds and polymers.

BacLight LIVE/DEAD® bacterial viability assays were conducted with bacteria *K. pneumoniae* (Gram-negative) and *S. aureus* (Gram-positive) exposed to compound 3 of FIG. 8. In this assay, bacterial cells were stained using Syto-16 and propidium iodide, to distinguish live (green fluorescence) from dead (red fluorescence) cells using confocal scanning laser microscopy (CSLM). Results showed that the majority of *S. aureus* and *K. pneumoniae* cells were alive (i.e. green fluorescence) in controls, but dead (i.e. red fluorescence) when exposed to compound 3. The morphology of *S. aureus* and *E. coli* cells exposed to 3 and 4 was also observed by field emission scanning electron microscopy (FE-SEM). FE-SEM micrographs indicated the disruption of cell membrane and subsequent killing of bacterial cells by absorption of 3 and 4.

Haemolysis of mouse red blood cells (RBCs) was evaluated after incubation with resin acid-derived compounds 2, 3 and polymer 4 (FIG. 8). The HC50 (haemolytic concentration that resulted in 50% haemolysis of RBCs) of compound 2 was higher than 860 µM. Interestingly, compound 3 displayed a HC50 of 162 µM, however, a further increase in concentration to 810 µM did not induce the increase of haemolysis level. Polymer 4 showed that the HC50 was much higher than 30 µM. The high selectivity was manifested by the high ratios of HC50 to MIC, which were at least 21-500, 6-100, and 6-44 for compound 2, compound 3 and polymer 4 respectively. This indicated that our antimicrobial materials are capable of selectively lysing microbial membranes, rather than mammalian cells.

In conclusion, novel quaternary ammonium-containing antimicrobial compounds and polymers have been developed, which utilized natural resin acids as an active hydrophobic component. These antimicrobial materials possessed excellent antimicrobial activity and high selectivity against bacteria over mammalian cells. It was suggested that the high antimicrobial activity was due to the hydrophobicity and unique structure of natural resin acids.

As such, this work shows the potential for many other compound and polymer systems to be applied in a similar fashion to obtain controlled properties. The strategy described here not only offers the diversity of structures of different compound and polymer systems, but also tailored properties. It is envisioned that the successful implementation of this strategy will enable rosin-containing cationic compounds and polymers to replace some petrochemical based compounds and polymers in a variety of areas.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A method of forming rosin-derived cationic compound, the method comprising:
   attaching a cationic group to a conjugated diene on a hydrophenathrene-based ring of a resin acid to form a rosin-derived cationic compound, wherein the rosin-derived cationic compound comprises a carboxylic acid group; and
   reacting the carboxylic acid group on the rosin-derived cationic compound with a polymerizable group to form a functionalized rosin-derived cationic compound having a polymerizable functional group.

2. The method as in claim 1, wherein the resin acid comprises levopimaric acid, abietic acid, dehydroabietic acid, or a mixture thereof.

3. The method as in claim 1, wherein attaching the cationic group to the conjugated diene on the hydrophenathrene-based ring of the resin acid comprises: reacting a dienophile with the hydrophenathrene-based ring of the resin acid via a Diels-Alder reaction.

4. The method as in claim 1, further comprising:
   polymerizing a plurality of the functionalized rosin-derived cationic compounds having a polymerizable functional group via controlled polymerization into a polymeric material, wherein each polymer defines a functional end group, and wherein the polymeric material has a polydispersity index of about 1 to about 1.5.

5. The method as in claim 4, wherein the polymer has a polydispersity index of about 1.05 to about 1.45.

6. The method as in claim 4, wherein the polymerizable functional group comprises a vinyl group.

7. The method as in claim 6, wherein the functional end group comprises a vinyl group.

8. The method of claim 6, further comprising:
   reacting the carboxylic acid group on the rosin-derived cationic compound with an amine to form the functionalized rosin-derived cationic compound having the vinyl functional group.

9. The method of claim 6, further comprising:
   reacting the carboxylic acid group on the rosin-derived cationic compound with an alcohol to form the functionalized resin acid having a vinyl functional group.

10. The method of claim 9, wherein the alcohol comprises a hydroxyalkyl (meth)acrylate.

11. The method of claim 6, wherein the alcohol comprises a hydroxyalkyl methacrylate.

12. The method of claim 6, wherein the plurality of rosin-derived cationic compounds is polymerized via controlled living polymerization.

13. The method of claim 12, wherein the controlled living polymerization comprises atom transfer radical polymerization, wherein the rosin-derived cationic compounds are polymerized in a polymerization solution comprising the rosin-derived cationic compound, an initiator, a ligand, and a catalyst.

14. The method of claim 13, wherein the initiator comprises an organic halide.

15. The method of claim 14, wherein the organic halide comprises an alkyl halide.

16. The method of claim 13, wherein the catalyst comprises copper(I).

17. The method of claim 12, wherein the controlled living polymerization comprises reversible addition-fragmentation chain transfer polymerization, wherein the rosin-derived cationic compounds are polymerized in a polymerization solution comprising the rosin-derived cationic compound, an initiator, and a chain transfer agent.

18. The method of claim 17, wherein the initiator comprises azobisisobutyronitrile, 4,4'-azobis(4-cyanovaleric acid), or combinations thereof.

19. The method of claim 17, wherein the chain transfer agent comprises a thiocarbonylthio compound.

\* \* \* \* \*

UNITED STATES PATENT AND TRADEMARK OFFICE
CERTIFICATE OF CORRECTION

| | | |
|---|---|---|
| PATENT NO. | : 8,604,128 B2 | Page 1 of 1 |
| APPLICATION NO. | : 13/396877 | |
| DATED | : December 10, 2013 | |
| INVENTOR(S) | : Tang et al. | |

It is certified that error appears in the above-identified patent and that said Letters Patent is hereby corrected as shown below:

On the Title page, Item (56) under Other Publications, col. 2, line 1, Gabriel et al., "Infectious disease: connecting inate..." should read --infectious disease: connecting innate--;

In the claims,

Column 20, Line 7, "The method of claim 6..." should read --The method of claim 9...--.

Signed and Sealed this
Twenty-first Day of April, 2015

Michelle K. Lee
*Director of the United States Patent and Trademark Office*